United States Patent [19]

Gillis

[11] E Patent Number: Re. 33,252

[45] Reissued Date of Patent: Jul. 3, 1990

[54] HYBRIDOMA ANTIBODY WHICH INHIBITS INTERLEUKIN 2 ACTIVITY

[75] Inventor: Steven Gillis, Mercer Island, Wash.

[73] Assignee: Immunex Corporation, Seattle, Wash.

[21] Appl. No.: 889,102

[22] Filed: Jul. 23, 1986

Related U.S. Patent Documents

Reissue of:

[64] Patent No.: 4,473,493
Issued: Sep. 25, 1984
Appl. No.: 309,173
Filed: Oct. 7, 1981

U.S. Applications:

[63] Continuation-in-part of Ser. No. 258,601, Apr. 29, 1981, Pat. No. 4,411,993.

[51] Int. Cl.[5] ..... C12P 21/00; C12N 15/00; C12N 5/00; A61K 39/395; C07K 15/00; G01N 33/53

[52] U.S. Cl. ..... 530/387; 435/172.2; 435/240.26; 435/240.27; 435/70.21; 424/85.8; 436/548; 935/104

[58] Field of Search ..... 435/68, 172.2, 240.1, 435/240.2, 240.26, 240.27, 172.3; 424/85, 85.8; 530/387; 436/548; 935/104

[56] References Cited

U.S. PATENT DOCUMENTS 4,196,265 4/1980 Koprowski et al. ..... 435/2
4,411,993 10/1983 Gillis ..... 435/68

OTHER PUBLICATIONS

Stadler et al; "Charge Heterogeneity of Human Interleukin 2 (IL 2) and Inhibition of IL 2 Activity by Supernatant of Hybridomas Generated from Spleen Cells Immunized with IL 2", Fed. Proc. 40 (3 part II), 1111, Abstr. No. 5002 (1981).

Luben et al; "Production of Hybridomas Secreting Monoclonal Antibodies Against the Lymphokine Osteoclast Activating Factor", 154 *Journal of Clinical Investigation*, 1262, 64: 337 (1979).

Luben et al., "Use of in vitro Immunization in Production of Monoclonal Antibodies Against Osteoclast-Activating Factor: A Method with General Applicability to Lymphokines" in *Biochemical Characterization of Lymphokines*, 1979, DeWeck et al (ed.), Academic Press, New York, beginning at p. 321.

Kohler and Milstein, "Continuous Cultures of Fused Cells Secreting Antibody of Predefined Specificity", *Nature* 256:497 (1975).

Gillis, et al., "Long Term Culture of Tumour-Specific Cytotoxic T Cells", *Nature* 268:154 (1977).

Gillis, et al., "T Cell Growth Factor: Parameters of Production and a Quantitative Microassay for Activity", *J. Immunol.* 120:2027 (1978).

Watson, et al., "Biochemical and Biological Characterization of Lymphocyte Regulatory Molecules-I. Purification of a Class of Murine Lymphokines", *J. Exp. Med.* 150:849 (1979).

Gillis, et al., "Biochemical Characterization of Lymphocyte Regulatory Molecules-II. Purification of a Class of Rat and Human Lymphokines", *J. Immunol.* 124:1954 (1980).

Gillis and Watson, "Biochemical and Biological Characterization of Lymphocyte Regulatory Molecules V. Identification of an IL-2 Producing Human Leukemia T Cell Line", *J. Exp. Med.* 152:1709 (1980).

Gillis and Watson, "Functional Activity and Biochemical Characterization of IL-2 Produced by Murine Tumor Cell Lines", *Behring Inst. Mitt.* 67:48 (1980).

*Primary Examiner*—James Martinell

[57] ABSTRACT

A process for producing anti-IL-2 antibody from hybridoma cells generated by fusing activated, IL-2 immunized, murine lymphocyte cells with neoplastic murine myeloma cells. Fusion is accomplished by mixing the two cell lines together in the presence of a fusing agent. After fusion, the hybridoma cells are cultured in vitro in a supplemented tissue culture medium to thereby produce anti-IL-2 antibody. Also, the hybridoma cells are cloned by a limiting dilution procedure to isolate even more potent sources of anti-IL-2 antibody. Anti-IL-2 antibody is then purified from either tissue culture medium conditioned by hybridoma cells, or from peritoneal ascites of mice challenged with hybridoma cells.

6 Claims, 4 Drawing Sheets

HYBRIDOMA ANTIBODY WHICH INHIBITS INTERLEUKIN 2 ACTIVITY

Matter enclosed in heavy brackets [ ] appears in the original patent but forms no part of this reissue specification; matter printed in italics indicates the additions made by reissue.

DESCRIPTION

CROSS REFERENCE TO RELATED APPLICATION

This is a continuation-in-part of my copending U.S. patent application Ser. No. 258,601, now U.S. Pat. No. 4,411,993, filed Apr. 29, 1981.

TECHNICAL FIELD

The present invention relates to an antibody which inhibits Interleukin 2 (hereafter "IL-2") (formerly known in the literature as "T cell growth factor" or "TCGF") activity and a process for preparing same, and more particularly to a process for producing murine anti-IL-2 antibody from hybrid cells formed by the fusing of murine myeloma cells with murine anti-IL-2 antibody producing B-lymphocytes.

BACKGROUND ART

IL-2 is a soluble protein which has been found to influence cell-mediated immune responses in mammals; and in the past, has been produced by stimulating mouse, rat or human lymphocytes with a T cell mitogen. The immune responses which have been attributed to IL-2, include: (i) enhancement of thymocyte mitogenesis; (ii) production of alloantigen-directed cytotoxic T lymphocytes in spleen cell thymocyte and athymic nude mouse spleen cell cultures; (iii) promotion of long term in vitro proliferation of antigen specific helper or killer T cell lines; and (iv) promotion of anti-erythrocyte (red blood cell) plaque forming cell responses in nude mouse spleen cell cultures stimulated with sheep red blood cells.

From its ability to influence T cell dependent immune responses in vitro, it is thought that IL-2 plays a significant role in cell mediated immunity in vivo. The study of the in vivo capabilities of IL-2 has been hindered by the lack of reagents which are capable of detecting the presence of IL-2 serologically, as opposed to having to monitor its biological effect. Moreover, further examination not only of the molecular properties of this immunoregulatory molecule, but also of the biochemical comparisons between IL-2 and other lymphokine activities would benefit from the development of antibodies which react with IL-2. Accordingly, a principal object of the present invention is to develop a process for preparing an antibody which inhibits IL-2 activity which may be used to detect serologically its presence.

DISCLOSURE OF THE INVENTION

The present invention relates to a process for producing anti-IL-2 antibody from murine hybridoma cells. The process includes fusing anti-IL-2 antibody producing murine B-lymphocytes with murine myeloma cells and then cultivating the resulting hybrid cells by either culturing the hybrid cells in vitro in a selective medium to thereby liberate an anti-IL-2 antibody containing supernate or growing the hybrid cells in vivo by intraperitoneal injection of mice with the hybrid cells to thereby generate high concentrations of anti-IL-2 antibody. Prior to the fusion process, murine splenocytes, which previously have been immunized in vivo to rat IL-2, are activated by culturing the cells in vitro in a tissue culture medium containing a B cell mitogen. In the fusion process, the stimulated anti-IL-2 antibody producing cells are mixed with myeloma murine driver cells and then a fusing agent is added thereto. When cultivating the resulting fused cells by culturing, the cell mixture is cultured in a medium supplemented with selective compounds which prevent the growth of unfused driver cells. The process of the present invention results in hybrid cells which exhibit both the anti-IL-2 antibody generating capacity of the activated B-lymphocytes and the immortality of the drug-marked myeloma cells.

The process of the present invention also includes cloning the murine anti-IL-2 antibody producing hybrid cells by suspending single cell samples of the hybrid cells in vitro in a tissue culture medium. After the single cell cultures have grown to appropriate densities, the cells are resuspended in culture medium to continuously generate anti-IL-2 antibody.

The above-described hybridizing and anti-IL-2 antibody production process has been employed in conjunction with splenocytes harvested from BALB/c mice together with SP2/0AG14 hereafter "SP2") myeloma driver cells also from BALB/c mice. The anti-IL-2 antibody producing portion of the present invention has been carried out with hybrid cells generated by fusion of these two cell lines and by clones of such hybrid cells. Applicant has identified a particular clonal hybrid cell line, designated as 4E12B2D10, which is capable of significantly neutralizing IL-2 activity from murine, human and rat sources.

Tests conducted on the supernate generated by the hybrid cell lines produced by the present invention suggest that the anti-IL-2 antibody contained therein is a monoclonal B cell hybridoma whose immunoglobulin G product appears to be directed against a determinant present on molecules of human, murine and rat IL-2. This conclusion is based on the finding that passage of cloned hybrid cell culture supernatants through a Protein A-coupled Sepharose column yielded purified immunoglobulin G fractions which inhibited mouse, rat and human IL-2 activity. Secondly, hybridoma-derived IgG, in concert with lyophilized Staphylococcus aureus, was capable of precipitating both "cold" and intrinsically labeled IL-2 activity. Moreover, Sepharose conjugated with purified IgG fractions provided an extremely reactive IL-2 absorbtion matrix.

BRIEF DESCRIPTION OF THE DRAWINGS

The details of typical embodiments of the present invention will be described in connection with the accompanying drawings, in which.

BEST MODE OF THE INVENTION

Outline of Process

In accordance with the present invention, murine B lymphocytes, which previously have been immunized in vivo with rat IL-2, are activated by culturing the cells in vitro in a tissue culture medium which also contains a B cell mitogen. The mitogen stimulated lymphocyte cells are fused with malignant, murine myeloma cells by mixing the two different types of cells together and then pelleting the mixture. The cell pellet is then resuspended in a tissue culture medium which also contains a fusing agent. Thereafter, the cell solution is pelleted again and resuspended in another protein containing medium which is supplemented with various additives, feeder cells and selective suppressing agents precluding the growth of unfused myeloma cells thereby liberating an anti-IL-2 antibody producing hybrid cell. Alternatively, anti-IL-2 antibody may be expanded by injecting the hybridoma cells from the cell pellet into the peritoneal cavities of mice and thereafter collecting the interperitoneal ascites which contain high concentrations of anti-IL-2 antibody (see Example 3 below).

The present invention also concerns identifying potent anti-IL-2 antibody producing cell lines by cloning hybrid cell lines found to produce this antibody [contitutively] *constitutively*. Cloning is accomplished by a limiting dilution procedure wherein anti-IL-2 antibody producing hybrid cells are individually cultured in vitro in culture medium containing feeder cells and selective suppressing agents which prevent the growth of unfused myeloma cells.

In the process of the present invention, BALB/c female mice have been utilized as a source of anti-IL-2 antibody producing B-lymphocytes. Activated spleen cells from these IL-2 immunized mice have been fused with the SP2 murine myeloma cell line, also derived from BALB/c mice, to produce several hybrid cell lines capable of constitutive anti-IL-2 antibody production (see FIG. 1). Cloning of one of the most potent IL-2 inhibitor cell lines, denominated as 4E12, has resulted in the identification of various clonal hybrid cell lines which are capable of producing anti-IL-2 antibody, including a cell line labeled as 4E12B2. An even more potent antibody source, designated as 4E12B2D10, has been isolated by subcloning the 4E12B2 clonal cell line. Samples of the 4E12, 4E12B2 and 4E12B2D10 are on deposit with the American Type Culture Collection, 12361 Parklawn Drive, Rockville, Md. 20852, under accession numbers HB8093, HB8092, and HB8091, respectively.

Figure 1:
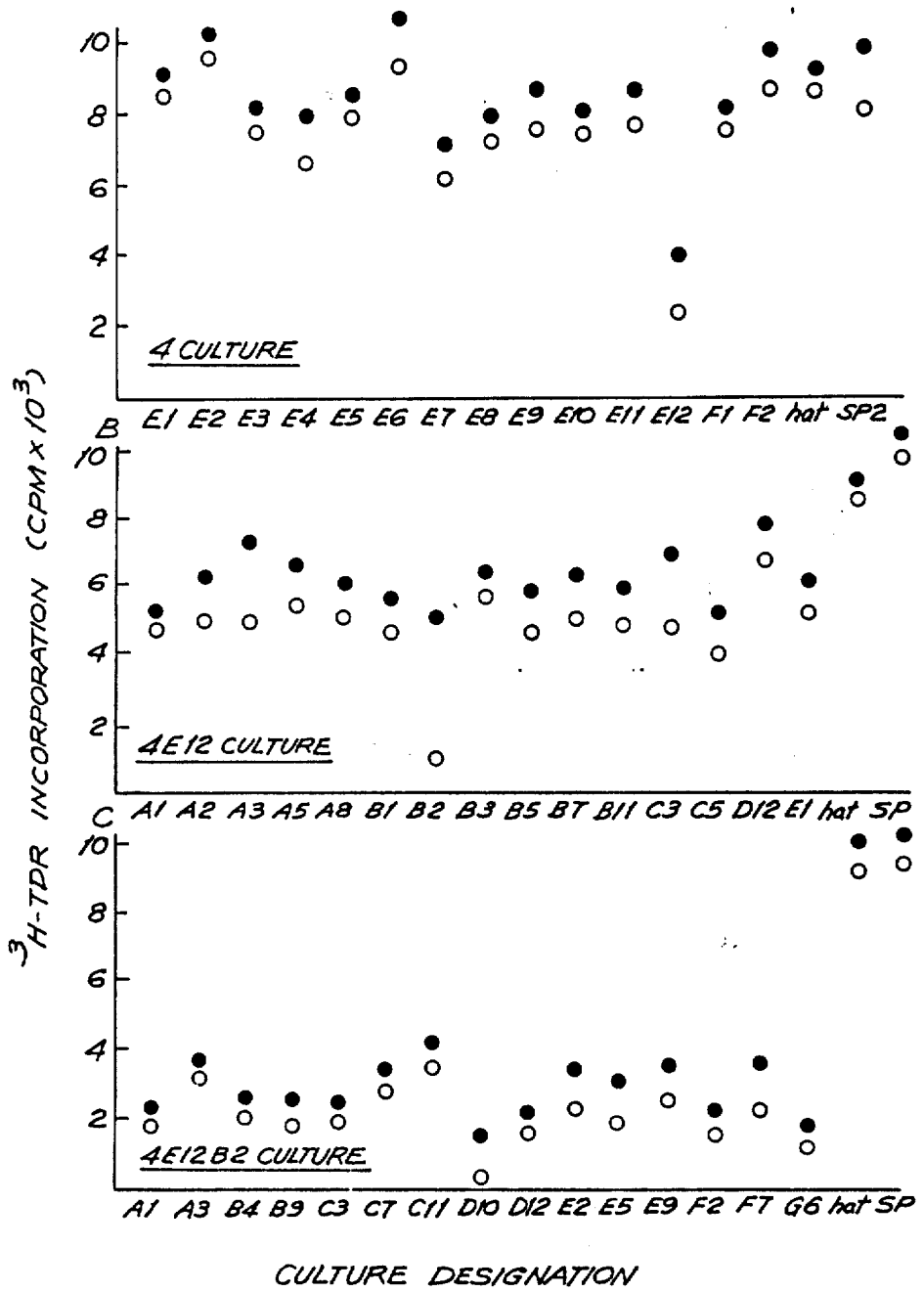
FIG. 1 shows the results of neutralization (●) and precipitating (○) screening trials monitoring the isolation of the parent cell line, designated as "4", and the 4E12, 4E12B2 and 4E12B2D10 clonal cell lines.

The effectiveness of the anti-IL-2 antibody produced by the parent and clonal cell lines, set forth above and in FIG. 1, may be ascertained by testing the capacity of the antibody to inhibit the ability of IL-2 to induce effector T cell replication. In the test procedure, the supernate produced by the hybrid cells of the present invention are mixed with cytotoxic T lymphocytes (hereafter "CTLL") in a supplemented tissue culture medium containing IL-2. The CTLL cells which proliferate under the stimulation of IL-2 will incorporate tritiated thymidine (hereafter "[$^3$H]Tdr") whereas cells which are cultured in the absence of IL-2 will incorporate only control levels of [$^3$H]Tdr. Thus, in FIG. 1, the lower the level of [$^3$H]Tdr incorporation, the more effectively the antibody produced by a particular cell line inhibits IL-2 activity.

FIG. 1 shows the results of neutralization (●) and precipitating (○) screening trials monitoring the isolation of the 4E12B2D10 hybridoma. In the initial plate "4" culture (panel A) only microwell culture 4E12 produced supernate which significantly inhibited IL-2 dependent CTLL cell [$^3$H]Tdr incorporation. Subsequent limiting dilution cloning gave rise to the hybrid cell lines screened in panel B of which the line designated 4E12B2 produced the most inhibitory supernate. Additional subcloning and screening results (panel C) show that all 4E12B2 daughter clones produce supernates which markedly inhibit IL-2 dependent proliferation in neutralizing the precipitating screening cultures.

As outlined above, in the anti-IL-2 antibody production process of the present invention, prior to fusion, BALB/c mice are immunized with IL-2 and antibody producing B-lymphocytes harvested from their spleens. Preferably the immunization is conducted periodically, and in various amounts to induce in vivo generation of anti-IL-2 activity. Ideally the immunizations are conducted weekly for four weeks in 3000 unit doses. Rather than utilizing IL-2 singularly, it may be mixed with complete or incomplete Freunds adjuvant. Also, rather than injecting the entire volume of IL-2 in one body location, preferably on each occasion multiple injections are placed about the body of the mice, for instance in the hind legs and in the peritoneal cavity.

Also, according to the present invention, prior to fusion, spleen cells from the IL-2 [ummunized] *immunized* mice are removed and single cell suspensions prepared therefrom. The splenocytes are cultured in a tissue culture medium supplemented with various additives. A B cell mitogen is added to the culture medium to activate the "immune" spleen cells, prior to fusion.

In the process of the present invention IL-2 is employed to induce murine splenocytes to produce anti-IL-2 antibody. As discussed more fully below, IL-2 is also employed in a process for screening hybridoma supernate samples for their capacity to inhibit IL-2 activity. IL-2 for these uses may be produced by culturing murine splenocytes, or particular murine thymoma (LBRM-33) or human leukemia (Jurkat-FHCRC) cells in vitro in a protein containing medium supplemented with various additives. A T cell mitogen is added to the culture medium to stimulate production of supernate which contains IL-2. After a period of time, the supernate is collected and processed to purify the IL-2 into a more concentrated form, for instance, by sequential ammonium [sulphate] *sulfate* precipitation, gel exclusion chromatography, ion exchange chromatography, and preparative flat-bed iso-electrical focusing.

Different types of murine myeloma cells may be fused with the activated antibody producing splenocytes to thereby infuse the hybrid cells with the ability to proliferate after fusion. One such driver drug-marked myeloma cell line is the SP2 myeloma cell derived from the BALB/c mouse. Additional driver cell lines include NS-1, P3, XC3, Ag8 and other drug-marked BALB/c mouse myeloma cell lines.

The fusion step of the present invention includes combining driver myeloma cells with activated anti-IL-2 antibody producing cells by first mixing the cells and then pelleting them by centrifugation. Thereafter, the cell pellet is suspended in a slightly alkaline tissue culture medium which also contains a fusing agent that facilitates fusion of the two different types of cells. Fusing agents may include various types of condensation polymers of ethylene oxide and water, such as polyethylene glycol (hereinafter "PEG") 1500. Other fusing agents include deoxyribonucleic acid (hereinafter "DNA") transforming viruses, such as Sendai virus or the fusion protein obtained therefrom. For optimum fusion, the quantity and concentration of the fusing agent must be controlled. For instance, if PEG 1500 is used to fuse immunized BALB/c mice splenocytes with SP2 myeloma cells, this fusing agent should comprise about 40% (weight/volume). However, the volume of PEG 1500 may range from 0.5 to 3 milliliters and the concentration of PEG 1500 may vary from 35% to 60% weight/volume of culture medium.

The process of the present invention involves several culturing procedures, including during: (i) production of IL-2 for use in (a) immunizing animals to allow for in vivo generation of the anti-IL-2 antibody producing cells, and (b) screening hybridoma supernates for their capacity to inhibit IL-2 activity; (ii) initial activation of the parent, anti-IL-2 antibody producer cells with a B cell mitogen prior to hybridization; (iii) fusion of anti-IL-2 antibody producer cells with drug-sensitive myeloma cells; (iv) cloning and subcloning of hybridoma antibody producer cells; (v) anti-IL-2 antibody production by parent and clonal hybrid cells; and (vi) screening, concentrating and purifying the anti-IL-2 antibody present in the hybridoma supernates. Various types of appropriate cell culturing media, which have been previously found to foster growth of murine lymphocyte cells, may be utilized in these different culturing steps. The culture media include Roswell Park Memorial Institute (hereafter "RPMI") 1640 medium, Click's medium, and Dulbecco's Modified Eagle's medium (hereafter "DMEM").

In the production of anti-IL-2 antibody containing supernates from the parent and clonal hybridoma cells, the culture media may be supplemented with various individual additives or combination of additives, including fetal calf serum (hereafter "FCS"), which has been heat-inactivated by, for example, applying heat at 56° C. for approximately 30 minutes. The quantity of FCS added may be from 5 to 20% of the total culture volume. Another additive is penicillin at a concentration range of approximately 25 to 250 units per milliliter, and preferably approximately 50 units per milliliter. Streptomycin also may be utilized as an additive in a preferred concentration range of from 20 to 250 micrograms per milliliter of total culture volume, and ideally approximately 50 micrograms per milliliter. Further additives include: (i) sodium pyruvate in a concentration range of approximately 10 to 150 millimolar and ideally approximately 100 millimolar; (ii) N-2-hydroxypiperazine-XI[1]-2-ethene-sulfonic acid (hereafter "Hepe's") buffer in a preferred concentration of from 10 to 60 millimolar, and ideally approximately 25 millimolar; and (iii) fresh L-glutamine in a preferred concentration range of approximately 150 to 500 micrograms per milliliter, with an ideal concentration of approximately 300 micrograms per milliliter. In addition, $NaHCO_3$ in concentration range of 1 to 30 millimolar and ideally about 16 millimolar may be added to the culture media.

As discussed above, in the anti-IL-2 antibody production process of the present invention, prior to fusion, the antibody producer cells, such as the immunized BALB/c splenocytes, are activated with a B cell mitogen. Also, T cell mitogens are utilized in the culturing process to prepare rat IL-2 for use in immunizing the anti-IL-2 antibody producing cell line, such as the BALB/c mouse, and to prepare murine and human IL-2 for use in testing the ability of the anti-IL-2 antibody of the present invention to inhibit anti-IL-2 activity, discussed more fully below. T cell mitogens may include various commercially available standard plant glycoproteins, such as phytohemagglutinin (hereafter "PHA"), concanavalin A (hereafter "Con A") and pokeweed mitogen (hereafter "PKM"). Although different concentrations of a particular mitogen may be employed, applicant has found that if PHA is used, a concentration of approximately 1% by volume is sufficient to stimulate some murine (LBRM-33) and human malignant (Jurkat-FHCRC) cell lines into IL-2 production. If Con A is employed to stimulate mouse or rat IL-2 production, approximately 5 micrograms per milliliter of culture medium should be utilized.

In the stimulation of harvested murine spleens prior to fusion, the splenocytes may be activated with the B cell mitogen E. Coli lipopolysacchride (hereafter "LPS") or with PKM. If LPS is employed, ideally it can be added in a concentration of about 20–100 micrograms per milliliter of culture medium.

During the process of culturing the hybridoma cells after fusion, parent myeloma cell growth inhibitors or suppressants such as hypoxanthine, aminopterin and thymidine (hereafter collectively referred to as "HAT") may be added to the culture medium to prevent unfused myeloma cells from proliferating. Hypoxanthine may be added in an [about] *amount* of 10 to 20 milligrams per liter of culture medium, and preferably about 13.6 milligrams per liter. Also, the concentration of aminopterin may be from 0.1 to 0.2 milligrams per liter of culture medium, and preferably about 0.176 milligrams per liter; and the concentration of thymidine may be from 3.0 to 4.5 milligrams per liter of culture medium and ideally about 3.88 milligrams per liter.

During the process of culturing the fused cells and the clones thereof, feeder cells may be added to the culture medium to induce proliferation of the cells. Although not yet definitely confirmed, it is considered that the feeder cells function to provide optimal cell density to allow small numbers of hybrid cells to multiply more readily. Also, it is thought that the feeder cells may provide the hybrid cells with nutrients required for their proliferation. Various types of feeder cells may be employed, including thymocytes from the BALB/c mouse. Other types of feeder cells include murine spleen cells, irradiated murine peritoneal exudate cells and murine macrophages. Although various concentrations of feeder cells may be added to the culture medium, preferably the feeder cells should be added to the HAT containing cultures at concentrations ranging from 0.5 to $5\times10^6$ cells/milliliter with an optimum density of about $3\times10^6$ cells per milliliter.

The different culturing steps of the present invention, discussed above, may be carried out in various environmental conditions. Preferably, however, the cultures should be maintained at a temperature range of approximately 35° to 38° C. and in a humidified atmosphere of approximately 5 to 10% $CO_2$ in air. Also, ideally the pH of the culture medium should be kept in slightly alkaline condition, in a range of approximately pH 7.2 to 7.4.

As briefly mentioned above, the present invention also includes identifying potent sources of anti-IL-2 antibody by cloning hybrid cell lines known to produce significant quantities of anti-IL-2 antibody. Thereafter, the cloned hybrid cell lines are cultured in a medium supplemented with various additives in substantially the same manner in which anti-IL-2 antibodies are produced by hybrid 4E12 cells, as outlined above. Cloning is accomplished by a limiting dilution procedure wherein the more potent parent hybrid cells, such as 4E12 cells, are cultured in flat-bottomed microplate wells. The hybrid cells are individually seeded in 200 microliter volumes of fresh Click's medium supplemented with 15% by volume FCS, 100 millimolar sodium pyruvate, 13.6 milligrams per liter hypoxanthine, 0.176 milligrams per liter aminopterin, and 3.88 milligrams per liter of thymidine, (hereafter collectively referred to as "HAT medium"). Feeder cells, such as thymocytes from the BALB/c mouse in a preferred concentration of approximately $3-6\times10^6$ cells per milliliter of culture medium, are added to facilitate cell growth. After approximately one week in culture, the microplate wells are examined microscopically for cultures containing single clusters of hybrid cell growth. Once identified, these growth cultures are fed every three days with 100 microliters of fresh HAT medium. After the hybrid cell populations reach 50 to 70% confluence, the supernate samples produced thereby are assayed for anti-IL-2 reactivity.

The clonal cell lines which produce the highest titers of anti-IL-2 antibody, such as the hybrid cell line designated in FIG. 1 as 4E12B2, are then subcloned to seek even more potent antibody generating cell lines. The technique followed for subcloning is the same as that used during the original cloning process. Use of this procedure to subclone the hybrid 4E12B2 cells has led to the identification of an even more potent anti-IL-2 antibody producing cell line, designated as 4E12B2D10. As illustrated in FIG. 1, the 4E12B2D10 cell line was found to produce even greater quantities of anti-IL-2 antibody than generated by the same numbers of 4E12B2 cells. After potent anti-IL-2 antibody producing hybrid clonal cell lines, such as the 4E12B2D10 cell line, are identified, they are expanded in HAT-free Click's medium to generate sufficient volumes of supernate to further characterize the antibody contained in the supernate. Alternatively, the potent anti-IL-2 antibody producing hybrid clonal cell lines may be expanded by injecting the cloned anti-IL-2 producing cells into the peritoneal cavities of mice and thereafter collecting the interperitoneal ascites, containing high concentrations of anti-IL-2 antibody, as explained more fully in Example 3 below.

Screening for anti-IL-2 antibody

The anti-IL-2 antibody produced by the hybridoma culture supernates of the parent and clonal hybrid cells of the present invention were screened to ascertain, for example, what cell lines produce significant levels of antibody. The screening process tested the ability of the antibody to prevent IL-2 dependent replication of effector cells harvested from long-term culture. The screening process was conducted both in the presence and in the absence of a complexing agent. Because hybridoma antibodies are usually incapable of forming large precipitating complexes, screening in the absence of a complexing agent would only detect neutralizing antibodies which are reactive against determinants present on, or near, the active site of IL-2. However, if a complexing agent is utilized, the screening process, in addition to detecting neutralizing antibodies, would also disclose antibodies that are directed against determinants elsewhere on the IL-2 molecule.

Briefly, the screening procedure includes suspending approximately $4\times10^4$ IL-2 dependent CTLL cells in 100 microliter volumes of Click's medium supplemented with 10% by volume FCS. Approximately 50 microliters of a one-fifth dilution hybridoma supernate and 50 microliters of rat IL-2 (0.5 units per milliliter IL-2 activity) containing conditioned medium are added to the suspension medium to thereby from 200 microliter volumes. Thereafter, either 50 microliters of FCS-supplemented Click's medium (neutralizing screening test) or 50 microliters of lyophilized Staphylococcus aureus (Igsorb, Enzyme Center, Inc., Boston, Mass.) (precipitating screening tests) are added to the culture. The precipitating screening cultures contain a 1/200 final dilution of the Igsorb reagent.

After 24 hours of culturing at 37° C. in a humidified atmosphere of 5% $CO_2$ in air, the screening cultures are pulsed for approximately 4 hours with 0.5 microcuries of tritiated thymidine (hereafter "[$^3$H]Tdr") (New England Nuclear, Boston, Mass.) having a specific activity of 20 millicurie per millimole. After pulsing, the cultures are harvested onto glass fiber filter strips, for instance, with the aid of a multiple automated sample harvester. [$^3$H]Tdr incorporation by the CTLL cells is measured by liquid scintillation accounting. By this procedure, the CTLL cells which are exposed to IL-2 incorporate significant amounts of (approximately 10,000–20,000 counts per minute) [$^3$H]Tdr. However, CTLL cells cultured in the presence of IL-2 and anti-IL-2 containing hybridoma supernate incorporates only scintillant control levels of [$^3$H]Tdr (approximately 80–200 counts per minute).

The amount of IL-2 used in screening procedures (approximately 0.5 units per culture) was determined by assay of standard IL-2 containing conditioned medium in a CTLL cell replication IL-2 microassay as discussed later.

Figure 2:
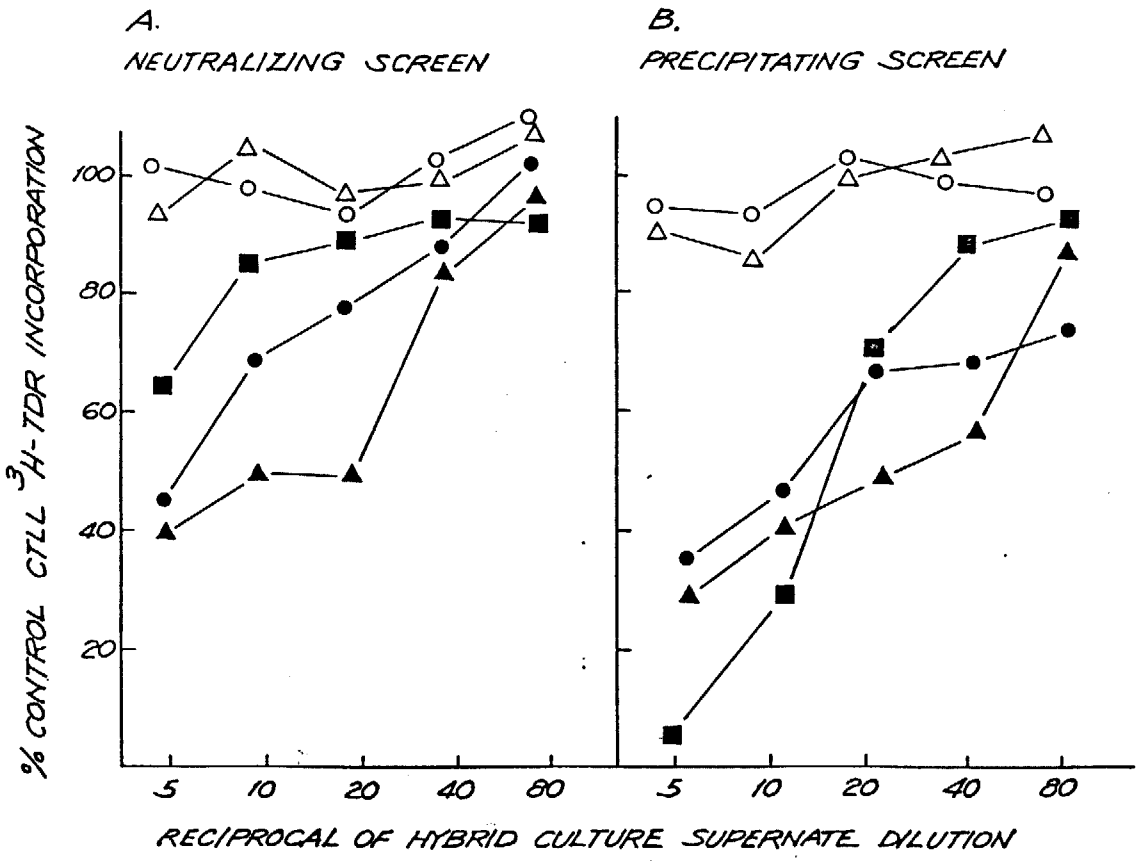
FIG. 2 shows the results of neutralization (A) and precipitating (B) screening cultures detailing the inhibitory effects (on IL-2 dependent CTLL cell proliferation) of supernates harvested from 4E12B2D10 (▲) 5G8H5C6 (■) and 2D4A7 (●) hybrid cell cultures.

The results of the screening tests are set forth in FIG. 1 above. Of the hybridomas in initial plate #4 (panel A), microwell culture 4E12 produced a supernate which significantly inhibited IL-2 dependent CTLL cell [$^3$H]Tdr incorporation in neutralizing screening tests. Moreover, the addition of [Ibsorb] *Igsorb* in the precipitation screening culture markedly increased the inhibitory capacity of the supernate. Subsequent limiting dilution clonings isolated the 4E12B2 hybridoma which also markedly inhibited IL-2 dependent proliferation in neutralizing and precipitating screening cultures (FIG. 1, panel B). The subcloning of this clonal hybridoma resulted in daughter clones, all of which produced supernates that significantly inhibited IL-2 activity (FIG. 1, panel C, and FIG. 2 below). This indicates that the subclone hybridomas, including the most inhibitory cell line, (4E12B2D10), are monoclonal.

FIG. 2 shows the results of neutralization (A) and precipitating (B) screening cultures detailing the inhibitory effects (on IL-2 dependent CTLL cell proliferation) of supernates harvested from 4E12B2D10 (▲), 5G8H5C6 (■) and 2D4A7 (●) hybrid cell cultures. No inhibition of IL-2 induced [$^3$H]Tdr incorporation was observed in identical screening assays which tested either HAT medium (Δ) or supernate harvested from SP2 myeloma cell cultures (○).

In all screening trials, the control cultures which utilized supernates harvested from the SP2 myeloma cultures did not mediate any inhibition of IL-2 induced CTLL cell proliferation, in either the neutralizing or precipitating screening trials; the SP2 conditioned medium test screening cultures incorporated from between 8 to $10\times10^3$ counts per minute of [$^3$H]Tdr. This same result was reached when HAT medium was substituted for the [hyrbridoma] *hybridoma* culture supernates in control experiments.

Fractionation of Anti-IL-2 Activity of Protein A Affinity Column Chromatography As discussed above, the observation that all 4E12B2 daughter cloned cells produced supernates which significantly inhibited IL-2 activity points to the monoclonality of these hybridomas. Further studies demonstrated that the anti-IL-2 activity present in the hybridoma supernates had a high affinity for protein A. Since it is known that protein A has a high affinity for the Fc portion of immunoglobulin G molecules, the affinity of the anti-IL-2 activity for protein A suggests that the anti-IL-2 inhibitory activity present in 4E12B2D10 hybridoma supernates is due to the presence of [a] *an* IgG antibody. As discussed above, the IgG was the product of single clones.

The procedure for fractionating the hybridoma supernates and then testing the inhibitory effect of the fractions on IL-2 activity[,] included precipitating protein present in 25 milliliters of 24 hour supernates harvested from 4E12B2D10 hybridoma cultures by slowly adding solid ammonium sulfate until a final saturation of 70% (weight/volume) was achieved. After overnight stirring of the mixture at 4° C., the protein precipitate was pelleted by a 20 minute centrifugation at 10,000× g. The resulting protein pellets were resuspended in as small a volume of sterile 0.9% NaCl (pH 7.2) as possible and then dialyzed for 24 hours against 1000 volumes of 0.9% NaCl. Three milliliters of the resulting dialyzed protein solution were applied to a column of Protein A Sepharose (Pharmacia Fine Chemicals, Piscataway, N.J.). The Sepharose column had been previously equilibrated in 0.9% NaCl (pH 7.2) and subsequently washed with additional 0.9% NaCl. The filtrate remaining from the Sepharose column was retained and tested for anti-IL-2 activity. To elute the hybridoma product which bound to the Protein A Sepharose matrix, the column was washed with 0.2 molar glycine HCl (pH3) buffer. The column acid wash (eluate) was then dialyzed against 100 volumes of 0.9 NaCl (pH 7.2) and followed by dialysis against 100 volumes of Hank's buffered salt solution (hereafter "HBSS").

Figure 3:
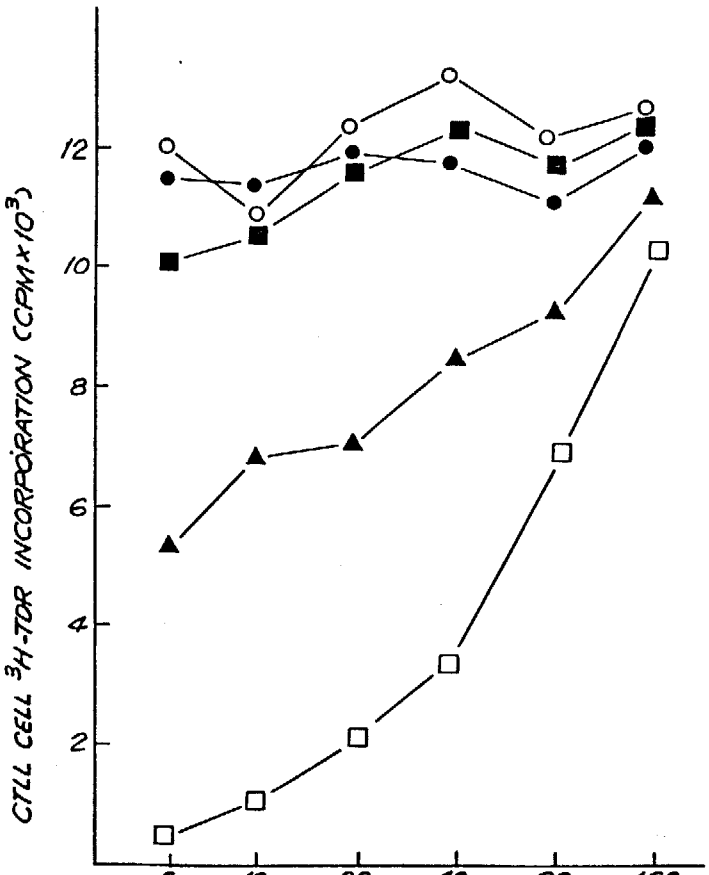
FIG. 3 shows Igsorb-precipitation screening cultures monitoring the anti-IL-2 effects of HAT medium (○), SP2 conditioned medium (●), supernate harvested from the clonal hybridoma 4E12B2D10 cell line (▲). The capacity of the 4E12B2D10 supernate to inhibit IL-2 dependent CTLL cell [$^3$H]Tdr incorporation was lost by passage of the supernate over a 3 ml column of Protein A conjugated Sepharose (■). However, enhanced anti-IL-2 inhibitory activity could be recovered from the column by standard acid elution using glycine-HCl (pH3) buffer and subsequent dialysis (□)

Thereafter, the eluate was tested for anti-IL-2 activity by use of the above-described precipitating screening culture. The filtrate remaining from the application of the hybridoma to the Protein A Sepharose column was also tested. As set forth in FIG. 3 below, the acid eluate solution exhibited pronounced anti-IL-2 activity whereas the filtrate did not. FIG. 3 also charts the capacity of the crude 4E12B2D10 supernate to inhibit IL-2 activity, as measured by its capacity to inhibit IL-2 dependent CTLL cell [$^3$H]Tdr incorporation. As in FIG. 2 above, FIG. 3 illustrates that both HAT medium and supernate harvested from SP2 myeloma cell culture had no capacity to inhibit IL-2 activity in screening assays.

In summary, the data set forth in FIG. 3 suggests that the anti-IL-2 inhibitory activity present in the 4E12B2D10 hybridoma supernate is due to the presence of a monoclonal (IgG) antibody which can be bound and eluted from a Protein A Sepharose column. Further, subtyping studies revealed that monoclonal anti-IL-2 was an IgG of the gamma $2_b$ subclass.

FIG. 3 shows Igsorb-precipitation screening cultures monitoring the anti-IL-2 effects of HAT medium (○), SP2 conditioned medium (●) and supernate harvested from the cloned hybridoma 4E12B2D10 cell line ([■] ). The capacity of the 4E12B2D10 supernate to inhibit IL-2 dependent CTLL cell [$^3$H]Tdr incorporation was lost by passage of the supernate over a 3 ml column of Protein A conjugated Sepharose ([□]■). However, enhanced anti-IL-2 inhibitory activity could be recovered from the column by standard acid elution using glycine-HCl (pH3) buffer and subsequent dialysis (□).

Inhibition of rat, mouse and human IL-2 activity by purified 4E12B2D10 hybridoma antibody By use of the above-described Igsorb precipitation tests, applicant has found that the 4E12B2D10 antibody, purified by the previously discussed Protein A Sepharose affinity procedure, has the ability to inhibit, equally effectively, rat, mouse and human IL-2 activity. As detailed in Table I below, two other hybridoma supernates, denominated as 5GBH5C6 and 2D4A7, exhibited this same ability. These results suggest that the antibodies isolated from the hybridoma supernates by Protein A Sepharose purification react with a determinant shared by all three species classes of IL-2.

TABLE I

Capacity of Hybridoma Antibody to Inhibit Mouse, Rat and Human IL-2 Activity in Precipitation Assays

| | Reciprocal of Supernate Dilution | | | | | | | | |
|---|---|---|---|---|---|---|---|---|---|
| | Mouse IL-2 | | | Rat IL-2 | | | Human IL-2 | | |
| | 1/10 | 1/20 | 1/40 | 1/10 | 1/20 | 1/40 | 1/10 | 1/20 | 1/40 |
| HAT Medium | 10.3[a](−11)[b] | 9.4(−1) | 9.0(4) | 9.3(0) | 9.2(1) | 8.9(4) | 9.9(−4) | 9.2(1) | 10.6(−13) |
| SP-2 conditioned medium | 9.1(4) | 9.5(−2) | 9.9(−4) | 9.2(1) | 9.3(0) | 9.3(0) | 9.8(−8) | 9.6(−3) | 9.7(−4) |
| 4E12B2D10 | 1.2(81) | 2.7(71) | 4.6(51) | 0.7(93) | 2.8(76) | 5.5(41) | 0.8(93) | 3.2(66) | 6.1(35) |

TABLE I-continued

Capacity of Hybridoma Antibody to Inhibit Mouse, Rat and Human IL-2 Activity in Precipitation Assays

| | Reciprocal of Supernate Dilution | | | | | | | | |
|---|---|---|---|---|---|---|---|---|---|
| | Mouse IL-2 | | | Rat IL-2 | | | Human IL-2 | | |
| | 1/10 | 1/20 | 1/40 | 1/10 | 1/20 | 1/40 | 1/10 | 1/20 | 1/40 |
| Protein A-Sepharose eluate 5G8H5C6 | 0.8(92) | 2.0(79) | 4.2(55) | 0.5(95) | 1.9(80) | 6.0(36) | 2.6(72) | 3.2(66) | 7.9(16) |
| Protein A-Sepharose eluate 2D4A7 | 0.3(97) | 1.5(84) | 3.5(63) | 2.8(70) | 3.0(68) | 4.9(48) | 1.3(87) | 4.3(54) | 5.6(40) |
| Protein A-Sepharose eluate | | | | | | | | | |

[a]cpm × $10^{-3}$CTLL$^3$H-Tdr incorporation.
[b]% inhibited of counted proliferation (9.3 × $10^3$ cpm of $^3$H-Tdr incorporated by 4,000 CTLL cells cultured in the presence of a 50% concentration of 1 U/ml rat IL-2).

The Igsorb precipitation procedure was essentially the same as that used during anti-IL-2 antibody screening protocols, as described above. Each of the culture samples contained approximately 4000 CTLL cells, 0.5 units per milliliter of IL-2 (regardless of the species source), a diluted quantity of eluted antibody and a 1/200 final dilution of Igsorb.

Rat IL-2 containing conditioned medium was prepared in the same manner as the IL-2 used to immunize the BALB/c female mice prior to hybridization, as set forth above. Mouse IL-2 containing conditioned medium was prepared by PHA (1% by volume, Grand Island Biologicals, Grand Island, N.Y.) stimulation of $10^6$ LBRM-33 mouse lymphoma cells per milliliter of conditioned medium. Human IL-2 containing conditioned medium was prepared by identical mitogen stimulation of (i) normal human splenocytes wherein $10^7$ splenocyte cells per milliliter of culture medium were utilized, or (ii) Jurkat-FHCRC human leukemic T cells wherein $10^6$ malignant cells per milliliter of culture medium were utilized.

Immune precipitation of IL-2 biological activity

Applicant has ascertained that the 4E12B2D10 derived antibody, IgG, after being removed from hybridoma supernate by the above-described Protein A Sepharose procedure, was capable of precipitating IL-2 activity. This finding supports the conclusion that the 4E12B2D10 culture consists of monoclonal B cells whose immunoglobulin G product appears to be directed against a determinant present on molecules of human, murine and rat IL-2.

In the precipitation procedure, individual 0.5 milliliter aliquots of: (i) SP2 conditioned medium; (ii) HAT medium, and (iii) a 1/20 dilution of Protein A Sepharose purified 4E12B2D10 IgG, were mixed in equal 0.5 volumes of rat conditioned medium containing 3.0 units per milliliter of IL-2. The mixtures were incubated in 15×75 millimeter glass centrifuge tubes for 30 minutes at 37° C. Thereafter 250 microliters of Igsorb (1/16 dilution in Click's medium) was added to each centrifuge tube and the incubation continued for an additional 45 minutes. After the incubation was completed, each sample was centrifuged for 20 minutes at 400×g and then the supernate samples assayed for residual IL-2 activity in standard IL-2 dependent CTLL [$^3$H]Tdr incorporation assays, as discussed below.

The results of the tests are set forth in FIG. 4 below. Only the test trials involving incubation of IL-2 activity with 4E12B2D10 antibody resulted in immune precipitation of rat IL-2 biologic activity. Similar pretreatment of rat IL-2 conditioned medium with equal volumes of either (i) medium conditioned by SP2 myeloma cells or (ii) HAT medium resulted in diminution of IL-2 activity titers corresponding only to the dilution caused by such addition.

Figure 4:
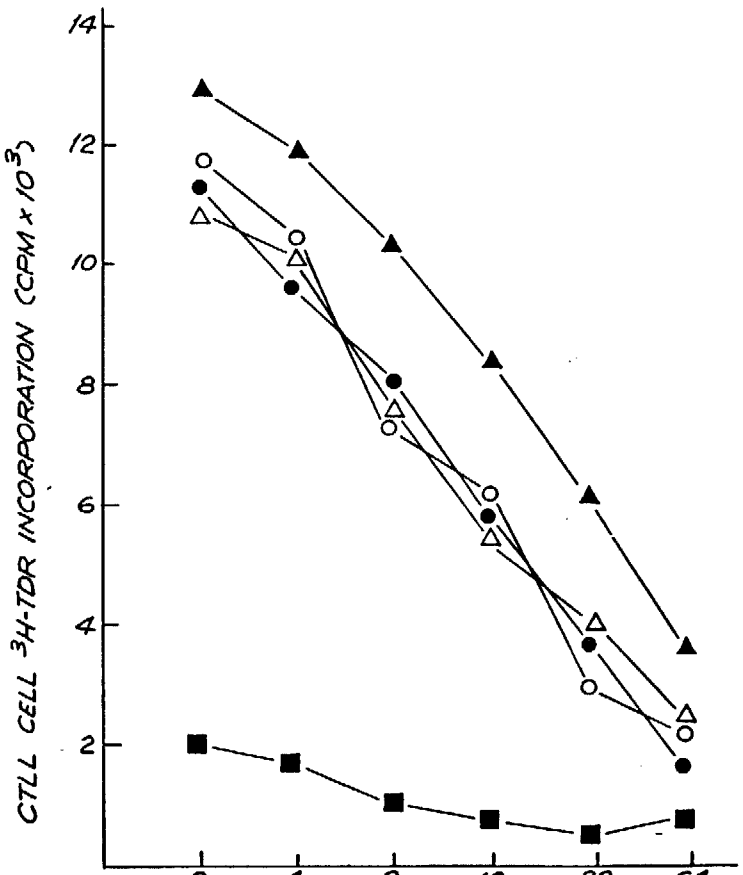
FIG. 4 shows the results of CTLL proliferation assays testing IL-2 activity remaining in the standard preparation of rat spleen cell condition medium (3 U/ml) either before (▲) or following Igsorb precipitation in the presence of Click's medium (Δ), SP2 condition medium (○), HAT medium (●), or Protein A Sepharose purified 4E12B2D10 IgG (■)

FIG. 4 shows the results of CTLL proliferation assays testing IL-2 activity remaining in standard preparation of rat spleen cell conditioned medium (3 U/ml) either before (▲) or following Igsorb precipitation in the presence of Click's medium (Δ), SP2 conditioned medium (○), HAT medium (●) or Protein A Sepharose purified [4E12B2D101gG] *4E12B2D10 IgG* (■). Only immune precipitation with 4E12B2D10 antibody resulted in a significant diminution of IL-2 activity beyond that demonstrated by dilution.

Immune precipitation of radio-labeled IL-2 activity

Applicant has determined that the 4E12B2D10 hybridoma antibody also has the ability to precipitate radio-labeled IL-2. This result not only confirms that the 4E12B2D10 supernate contains monoclonal B cell hybridomas having antibody products which are reactive with determinants present on the IL-2 molecule, but also provides the bases for a process by which the presence of IL-2 may be detected with less effort than required by conventional assay processes.

Prior to the actual precipitation process, biosynthetically $^3$H-labeled IL-2 activity was prepared by culturing the IL-2 producing murine tumor cell line, LBRM-33, in the presence of five different amino acids, each bearing a $^3$H-label, i.e. leucine, lysine, phenylalanine, proline and tyrosine (Catalog No. TRK550, Amersham Corp., Arlington Heights, Ill.). In the $^3$H-labeled IL-2 production process, 7×$10^5$ LBRM-33 cells per milliliter of culture volume were cultured in 25 milliliter volumes of RPMI 1640 medium supplemented with 2% by volume FCS. Each culture sample contained a deficient (20% of normal) concentration of each of the five amino acids. Also, at the beginning of the culture period, an additional amount of each particular amino acid, which previously had been tritium labeled, was added to the corresponding culture to achieve a final composite concentration of 10 microcuries per milliliter. After 48 hours of culture, the T cell plant mitogen, PHA, was added to each of the cultures in a final concentration of 1% by volume. Twenty-four hours later, the IL-2 containing supernates were harvested and then concentrated by 85% ammonium sulfate precipitation. Thereafter, the supernates were fractionated by sequential diethyl amino [ethly] *ethyl* (hereafter "DEAE") cellulose ion exchange chromatography and Sephadex G-100 gel exclusion chromatography as previously detailed in Gillis et al, "Biochemical and Biological Characterization of [Lympocytes] *Lymphocytes* Regulatory Molecules-II. Purification of a Class of Rat and Human Lymphokines", 124 The Journal of Immunology 1954 (1980). This process resulted in production of active fractions (20 to 100 units per milliliter) in the 33,000 to 36,000 molecular weight range, each containing considerable radio activity (approximately 100,000 counts per minute/milliliter) (see FIG. 5 below).

Figure 5:
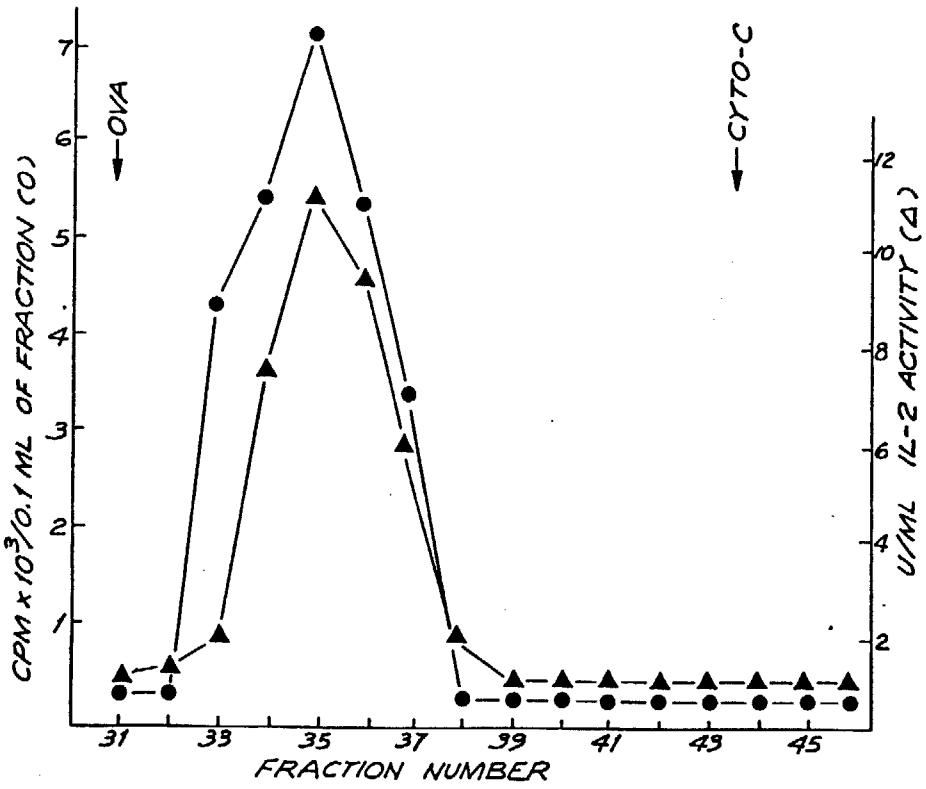
FIG. 5 shows IL-2 activity [()] (○) and cpm of $^3$H-label [(Δ)] (Δ) in Sephadex G100 fractions of biosynthetically radio-labelled LBRM-33 cell derived IL-2 preparations; and, FIG. 6 shows IL-2 activity present in 3 U/ml sample of rat spleen cell conditioned medium both prior to (Δ) and the following passage over a BSA conjugated [Sepherose] *Sepharose* column (●) or an identical column to which 4E12B2D10 IgG had been coupled (■).

FIG. 5 shows IL-2 activity (●) and cpm of $^3$H-label (▲) in Sephadex [G100] *G-100* fractions of biosynthetically radio-labeled LBRM-33 cell derived IL-2 preparations. Prior to gel exclusion chromatography, radio-labeled IL-2 present in LBRM-33 conditioned medium was concentrated by ammonium sulfate precipitation and DEAE ion exchange chromatography.

In the immune precipitation process itself, the $^3$H-labeled IL-2 containing fractions were diluted in Click's medium so that 20 microliter aliquots of the fractions each contained radioactivity levels of approximately 1200 counts per minute. The 20 milliliter aliquots were incubated at 37° C. in the presence of serial $\log_2$ dilutions of hybridoma supernate. Each supernate sample was placed in a sterile 15×75 milliliter glass centrifuge tube along with 10% by volume FCS-supplemented Click's medium collectively to compose 50 microliter volumes. The mixtures were incubated for 30 minutes at 37° C. in an atmosphere of 5% $CO_2$ in air. Thereafter, 20 microliters of Igsorb (½ dilution) [was] *were*added to each tube and the incubation continued for an additional 45 minutes. Then, 2 milliliters of 0.9% NaCl [was] *were* added to each tube and the immune precipitate pelleted by centrifuging for 5 minutes at 400×g. The pellet was washed twice in 2 milliliter volumes of 0.9% NaCl. After the final wash, 3.5 milliliters of Bioflour scintillation cocktail (New England Nuclear) [was] *were* added to each tube and the contents vortexed, prior to being transferred to plastic mini scintillation vials. Lastly, the tritium radioactive label associated with the pellet was counted by liquid scintillation. The counting results of the immune precipitation of $^3$H-labeled IL-2 activity are set forth in Table II, below.

TABLE II

Immune Precipitation of Radiolabeled IL-2 Activity.

| | CPM of $^3$H-IL-2 Associated with Igsorb Pellet[1] Supernate Dilution | | | | |
|---|---|---|---|---|---|
| Culture Supernate | 1/5 | 1/10 | 1/20 | 1/40 | 1/80 |
| HAT medium | 80 | 110 | 75 | 95 | 86 |
| SP-2 | 123 | 116 | 135 | 117 | 110 |
| 4E12B2D10 | 856 | 737 | 794 | 544 | 244 |
| 4E12B2D10 + XC Cold-IL-2 | 172 | 134 | 136 | 121 | 129 |
| 4E12B2D10 Protein A Sepharose-Acid Eluate | 186 | 245 | 615 | 775 | 892 |

[1]1200 cpm added to each reaction mixture

The same precipitation test was conducted using $\log_2$ serial samples of HAT medium, SP2 conditioned medium and a 1/5th dilution of the 4E12B2D10 hybridoma supernate, see Table II. It is interesting to note that the capacity of the 4E12B2D10 supernate to precipitate radio-labeled IL-2 remained at a high 794 count per minute level even when a 1/20 dilution of the hybridoma supernate was tested, and could be inhibited by performance of an identical immune precipitation in the presence of a 10-fold excess concentration of unradiolabeled IL-2.

4E12B2D10 IgG Affinity Chromatography

The conclusion that the 4E12B2D10 hybridoma cell line produces a monoclonal IgG antibody directed against some determinant present on the IL-2 molecule was further confirmed through tests which found that CNBr-mediated coupling of the hybridoma antibody to Sepharose 4B resulted in the preparation of a matrix capable of absorbing significant quantities of IL-2. This result indicates that the antibody generated by the present invention may be useful in affinity purification of biologically active IL-2.

The test procedure utilized included purifying by Protein A Sepharose affinity chromatography (as outlined above) concentrated hybridoma supernate from the 4E12B2D10 hybrid cell line. The antibody eluted from the Protein A Sepharose column chromatography purification procedure was diluted to a concentration of approximately 2 milligrams per milliliter in a coupling buffer composed of 0.5 molar NaCl and 0.1 molar $NaHCO_3$ (pH 8.3). The approximate antibody concentration was determined by ultraviolet light absorption (280 nM) using a Beckman Spectral photometer (using the assumption that [$E_{280}$[1]] *E'280*=10.0).

Prior to the addition of the purified antibody, one gram of the CNBr activated Sepharose 4B (Pharmacia Fine Chemicals[,] was swollen by washing with 200 milliliters of cold 1 millimolar HCl. The swollen Sepharose 4B was pelleted by centrifuging for 10 minutes at 200×g. Next, the activated CNBr Sepharose 4B was washed with 0.9 NaCl, resuspended in coupling buffer to form a 3 milliliter slurry and then the slurry mixed with 1 milliliter of 4E12B2D10 antibody in a 15 cubic centimeter conical centrifuge tube.

This was thereafter placed on an end over end shaker for 2 hours at room temperature to promote coupling of the antibody to the CNBr Sepharose 4B. Thereafter, the gel was pelleted and the excess unbound antibody removed. The CNBr active antibody sites which were left uncoupled by the above coupling process were blocked by resuspending the gel in 100 milliliters of 0.5 molar NaCl and 0.2 molar glycine (pH 8.0) buffer. The gel was again mixed for 2 hours on an end over end shaker.

As an additional control to ensure that any IL-2 activity removed by antibody-coupled Sepharose could not be due to direct coupling of the IL-2 to CNBr active Sepharose sites, a second CNBr Sepharose slurry was prepared. A 1 milliliter solution of 2 milligrams per milliliter of bovin serum albumin (hereafter "BSA") was coupled to this second slurry using the same coupling procedure as set forth above.

Both IgG and BSA coupled Sepharose gels, following treatment with 0.5 molar NaCl, 0.2 molar glycine (pH 8.0) buffer, were washed sequentially with three 10 milliliter volumes of coupling buffer, three 10 milliliter volumes of 0.1 molar sodium acetate buffer (in 0.5 molar NaCl, pH 4) and three additional 10 milliliter volumes of coupling buffer. Prior to use in IL-2 affinity [chromotography] *chromatography* trials, the columns equilibrated in sterile 0.9% NaCl (pH 7.2).

In the affinity trials, 10 milliliters of rat spleen cell conditioned medium, having an IL-2 activity level of 3 units per milliliter, were passed over each gel column. The resulting filtrates were collected and tested for residual IL-2 activity in standard IL-2 microassays, which as detailed below, monitored the IL-2 dependent [$^3$H]Tdr incorporation of CTLL cells. As set forth in FIG. 6 below, the filtrate collected from passage of the rat spleen cell conditioned medium over the BSA-conjugated Sepharose column contained as much IL-2 activity as that present in the original rat spleen cell-derived IL-2 solution. On the other hand, the filtrate collected after a single passage of the rat spleen cell conditioned medium over the column of 4E12B2D10 antibody-coupled Sepharose contained less than 5% of the IL-2 activity present in the original conditioned medium. The ability of anti-IL-2 antibody coupled to CNBr-Sepharose to absorb IL-2 activity further [cnfirms] *confirms* that a monoclonal antibody directed against some determinate present on the IL-2 molecule is produced by the 4E12B2D10 hybridoma cell line.

Figure 6:
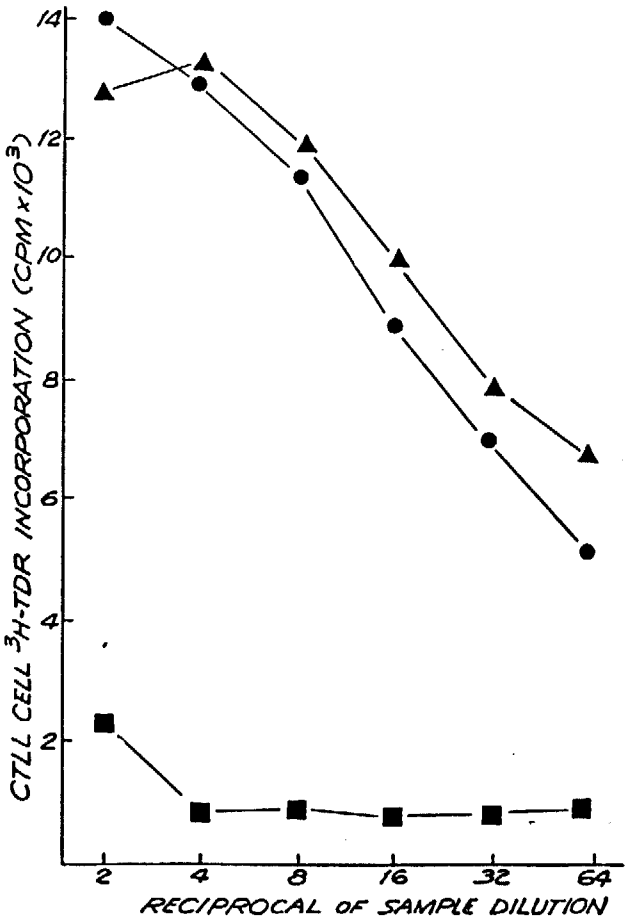

FIG. 6 shows IL-2 activity present in an 3 U/ml [sammple] *sample* of rat spleen cell conditioned medium both prior to (▲) and following passage over a BSA conjugated Sepharose column (●) or an identical column to which [4E12B2D101gG] *4E12B2D10 IgG* had been coupled (■).

Standard IL-2 Microassay

The IL-2 concentration in the above-described immune precipitation, affinity [chromotography] *chromatography*, and screening experiments (testing the effectiveness of the anti-IL-2 antibody produced by the parent and clonal cell lines) was determined by a conventional IL-2 microassay as outlined in Gillis et al. "T-Cell Growth Factor: Parameters of Production and a Quantitative Microassay for Activity", 120 The Journal of Immunology, 2027 (1978). Briefly, the assay procedure includes seeding approximately 4000 murine CTLL cells in a $\log_2$ dilution series of the given IL-2 sample. In each culture, the CTLL cells [ae] *are* suspended in Click's medium supplemented with 10% by volume FCS to thereby form 200 microliter total volumes. The cultures are incubated for approximately 12 hours at 37° C. in a humidified atmosphere of 5% $CO_2$ in air. Thereafter, the cultures are pulsed for approximately 4 hours with 0.5% microcurie of [$^3$H]Tdr having a specific activity of 20 microcurie per millimolar (obtained from New England Nuclear, Boston, Mass.).

After pulsing, the cultures are harvested onto glass fiber filter strips, for instance with the aid of a multiple automated sample harvested. [$^3$H]Tdr incorporation by the CTLL cells [as] *is* measured by liquid scintillation counting. By this procedure, the CTLL cells which are cultured in the presence of IL-2 will incorporate [$^3$H]Tdr in a dose dependent manner. On the other hand, CTLL cells cultured in the absence of IL-2 will incorporate only scintillant control levels of [$^3$H]Tdr and will be more than 95% trypan-blue positive after 24 hours of IL-2 deprivation, indicating that such cells are dead.

The concentration of IL-2 is quantified by probix analysis of thymidine incorporation data. A 1 unit per milliliter standard of IL-2 activity is defined as the amount of IL-2 activity present in a 48 [hours] *hour* tissue culture medium conditioned by Con A (5 micrograms/milliliter) stimulation of an initial concentration of $10^6$ normal rat spleen cells per milliliter of culture. A 1 unit per milliliter standard of IL-2 activity routinely stimulated approximately 10,000 counts per minute of [$^3$H]Tdr incorporation at a dilution of 1:2.

EXAMPLE 1

Six week old BALB/c female mice were immunized once weekly for four weeks with 3000 units of rat IL-2. The IL-2 used for the immunization program was prepared by stimulating a concentration of $1\times10^7$ rat splenocyte cells per milliliter of culture medium for 24 hours with 5 micrograms of Con A per milliliter of culture medium. The supernate produced thereby was purified sequentially by ammonium sulfate precipitation, Sephadex G-100 gel exclusion [chromotography] *chromatography*, DEAE cellulose ion exchange [chromotography] *chromatography* and preparative flat-bed iso-electric focusing, as described in Gillis et al., supra, 124 The Journal of Immunology 1954 (1980).

During each immunization, 1000 units of IL-2 in 0.2 milliliter volumes [was] *were* injected intradermally in each hind leg. Prior to the first immunization the IL-2 was mixed with complete Freund's adjuvant, and prior to the last three immunizations, the IL-2 was mixed with incomplete Freund's adjuvant. Also, during each immunization, 1000 units of rat IL-2, in a volume of 0.5 milliliters of 0.9% NaCl, [was] *were* injected intraperitoneally.

Two days prior to fusion, spleens from the IL-2 immunized mice were removed and single cell suspensions prepared therefrom. The splenocytes were cultured for 48 hours in Click's medium. The medium was supplemented with 10% by volume, heat-inactivated (56° C. for thirty minutes) FCS, 25 mM HEPES buffer, 16 mM $NaHCO_3$, 50 micrograms per milliliter of streptomycin, 50 units per milliliter penicillin and 300 micrograms per milliliter of fresh L-glutamine. The splenocytes were activated by adding 100 micrograms of E. Coli lipopolysaccharide per milliliter of culture. The culture was maintained at approximately 37° C. in a humidified atmosphere of 5% $CO_2$ in air.

Fusion was achieved by mixing approximately $8\times10^7$ of the LPS-activated "IL-2 immune" splenocytes with approximately $2\times10^7$ SP2 myeloma cells obtained from the BALB/c mouse. This cell line is a derivative of the SP2/HLGK myeloma line which does not constitutively produce immunoglobulin light chain. The cell mixture was pelleted by centrifuging for five minutes at 200×g. The resulting pellet was then immersed in a 37° C. water bath and carefully resuspended over a period of one minute with one milliliter of warm Click's medium ([PH] *pH* 7.3 and without FCS) containing 40% (weight/volume) polyethylene glycol 1500. Two more milliliters of warm, serum-free Click's medium were then added over the next two minute period. Thereafter, eight additional milliliters of this medium were added. Next, the mixture was centrifuged for five minutes at 200×g to complete the fusion process.

Constitutive production of anti-IL-2 antibody derived from the fusion of activated, IL-2 immunized, BALB/c splenocytes with SP2 myeloma cells was achieved by suspending the resulting cell pellet in 40 milliliters of Click's medium supplemented with 15% by volume FCS and 100 millimolar sodium pyruvate. The unfused myeloma driver cells were prevented from proliferating by the addition to the medium of 13.6 micrograms per liter of hypoxanthine, 0.176 micrograms per liter of aminopterin and 3.88 micrograms per liter of thymidine. The fused cell solution was then added to another 160 milliliters of the same medium which also contained approximately $8\times10^8$ BALB/c female mice thymocyte cells to serve as feeder cells. The entire cell suspension was gently mixed and then divided into 200 microliter aliquots in flat-bottomed microplate wells (No. 3596 Costar, Inc., Data Packaging, Cambridge, Mass.). The cultures were all maintained in approximately 37° C. in a humidified atmosphere of 5% carbon dioxide in air.

EXAMPLE 2

Anti-IL-2 antibody was constitutively produced by culturing approximately $10^6$ 4E12B2D10 clonal hybrid cells per milliliter of culture medium in either 2 milliliter volumes in cluster plates (No. 3524, Costar, Inc., Cambridge, Mass.) or in 10 milliliter volumes in culture flasks (No. 3013, Falcon Plastics, Oxnard, Calif.). The culture media contained Click's medium supplemented with 15% by volume, heat inactivated (56° C. for 30 minutes) FCS and 100 mM sodium pyruvate. The culture was maintained at approximately 37° C. in a humidified atmosphere of 5% $CO_2$ in air. Supernate harvested after 24 hours of culture contained approximately 5–15 micrograms/milliliter of anti-IL-2 Immunoglobulin G.

EXAMPLE 3

Anti-IL-2 antibody was produced in high concentration in vivo by intraperitoneal injection of BALB/c female mice with $10^6$ 4E12B2D10 hybridoma cells. One week prior to hybridoma cell injection, BALB/c mice were given 0.5 milliliter of pristane [intraperioneally] *intraperitoneally* as an ascites inducing irritant. From 14 to 17 days after hybridoma injection intraperitoneal ascites [was] *were* collected, and the anti-IL-2 Immunoglobulin G contained therein was purified by its affinity to Protein A-Sepharose.

As will be apparent to those skilled in the art to which the invention is addressed, the present invention may be carried out by using murine myeloma cell lines, culture media, culture media additives, T and B cell stimulants, fusing [atents] *agents* and cell growth inhibitors specifically disclosed above without departing from the spirit or essential characteristics of the invention. The particular processes described above are therefore to be considered in all respects as illustrative and not restrictive, i.e., the scope of the present invention is as set forth in the appended claims rather than being limited to the examples of the anti-IL-2 antibody producing processes as set forth in the foregoing description.

What is claimed is:

1. An anti-IL-2 antibody produced by:
immunizing murine B-lymphocyte cells with IL-2;
activating said immunized murine B-lymphocyte cells with a B-cell mitogen;
fusing said activated murine B-lymphocyte cells with murine myeloma cells;
[culturing] *cultivating* said hybridoma anti-IL-2 antibody producing cells under conditions suitable for antibody production; and
recovering the anti-IL-2 antibody produced by said anti-IL-2 antibody producing cells.

2. The anti-IL-2 antibody of claim 1, wherein said B-lymphocyte cells are from the BALB/c mice.

[3. The anti-IL-2 antibody of claim 1, wherein said hybridoma anti-IL-2 antibody producing cells include cells selected from the group consisting essentially of 4E12, 4E12B2 and 4E12B2D10 cells.]

*4. A monoclonal antibody that specifically binds IL-2, wherein said antibody is produced by a murine hybridoma which is the fusion product of a murine B lymphocyte and a murine myeloma cell.*

*5. A monoclonal antibody according to claim 4, wherein said antibody inhibits T-cell proliferation in the presence of interleukin-2.*

*6. A monoclonal antibody according to claim 4, wherein said antibody immunoprecipitates interleukin-2 molecules.*

*7. A monoclonal antibody produced by a cell line selected from the group consisting of ATCC HB8093, ATCC HB8092 and ATCC HB8091, and which specifically binds to IL-2.*

* * * * *